(12) United States Patent
Friedrich et al.

(10) Patent No.: US 6,437,198 B1
(45) Date of Patent: Aug. 20, 2002

(54) METHOD FOR PRODUCING ALKALI METAL ALCOHOLATES

(75) Inventors: Holger Friedrich, Bobenheim-Roxheim; Josef Guth, Freinsheim; Jürgen Schweinzer, Frankenthal; Thomas Letzelter, Annweiler; Hans-Jürgen Bender, Freinsheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/701,886

(22) PCT Filed: May 28, 1999

(86) PCT No.: PCT/EP99/03713

§ 371 (c)(1),
(2), (4) Date: Dec. 5, 2000

(87) PCT Pub. No.: WO99/65849

PCT Pub. Date: Dec. 23, 1999

(30) Foreign Application Priority Data

Jun. 12, 1998 (DE) .......................................... 198 26 394
May 5, 1999 (DE) .......................................... 199 20 594

(51) Int. Cl.$^7$ ................................................ C07C 31/30
(52) U.S. Cl. ...................................................... 568/851
(58) Field of Search ......................................... 568/851

(56) References Cited

U.S. PATENT DOCUMENTS 5,262,133 A    11/1993   Adams et al.
5,583,269 A    12/1996   Morrison et al.

FOREIGN PATENT DOCUMENTS

| DE | 1 251 297 | 10/1967 |
| DE | 2 333 634 | 10/1974 |
| DE | 26 12 642 | 9/1977 |
| DE | 298 502 | 2/1992 |
| EP | 192 608 | 8/1986 |
| EP | 749 947 | 12/1996 |
| EP | 810 193 | 12/1997 |
| FR | 805 126 | 12/1939 |
| JP | 05170680 | 7/1993 |

*Primary Examiner*—Alan Siegel
(74) *Attorney, Agent, or Firm*—Keil & Weinkauf

(57) ABSTRACT

The invention relates to a process for preparing alkali metal alkoxides by reacting alkali metals with alcohols in the presence of a catalyst, preferably a transition metal salt and especially iron(III) chloride.

16 Claims, 1 Drawing Sheet

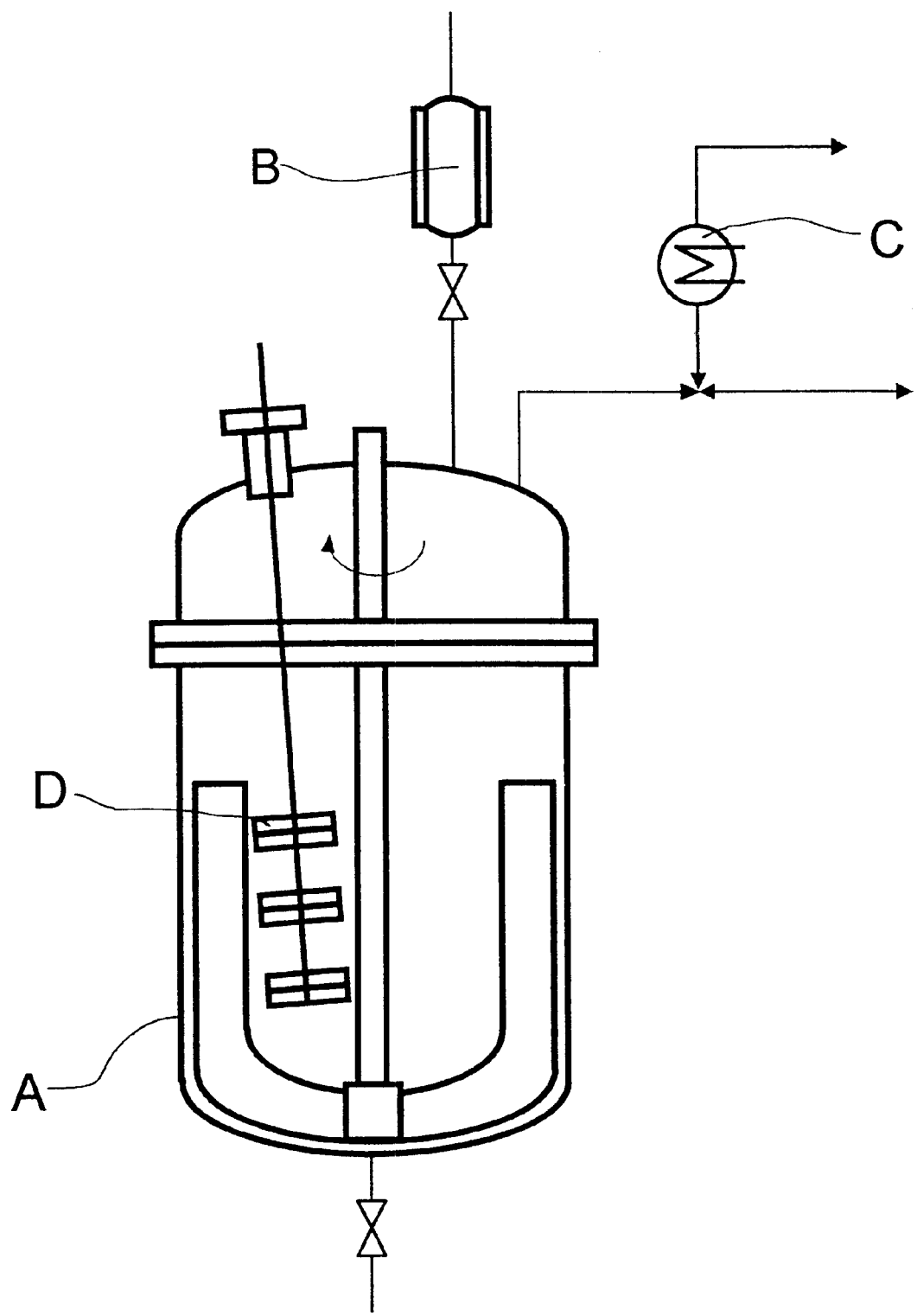

METHOD FOR PRODUCING ALKALI METAL ALCOHOLATES

This application is a 371 of PCT/EP99/03713 filed May 28, 1999.

The invention relates to a process for preparing alkali metal alkoxides, especially tertiary alkoxides such as sodium tert-butoxide.

The preparation of alkali metal alkoxides (also called alkali metal alcoholates) by reacting alkali metals with alcohols is common knowledge. In this reaction the chain length and the structure of the alcohol have a decisive influence on the reaction rate. The reaction rate decreases as the chain becomes longer and as the degree of branching in the alcohols goes up. Primary alcohols react very rapidly, whereas tertiary alcohols are extremely unreactive. The reaction of tertiary alcohols generally takes from several hours to several days.

A further factor is that, during the reaction, the saturation concentration of the respective alkoxide in the alcohol is frequently exceeded. The product precipitates and incrusts the alkali metal, so hindering it from further reaction. This is especially the case when the temperature is insufficient to melt the alkali metal and to allow its fine dispersion by stirring.

The low reaction rate causes problems in the implementation of the reaction. The achievable space-time yields are low, leading ultimately to high costs.

When the alkoxide is prepared, up to 3 mol of alcohol are bound as alcohol of crystallization per mole of alkoxide, depending on the preparation conditions. In some cases these alcohol-alkoxide complexes only crystallize out when the reaction is conducted in an inert solvent. As a result of the preparation-tied annexing of the alcohol of crystallization, the alkoxide becomes insoluble in numerous solvents. The alcohol of crystallization is difficult to eliminate from the alkoxides, and this may lead to unwanted side reactions in subsequent reaction steps. The aim is therefore to prepare alkoxides free from alcohol of crystallization within very short reaction times.

Various processes have been proposed for preparing alkali metal alkoxides, especially tertiary alkali metal alkoxides which are free from alcohol of crystallization, with a sufficient reaction rate.

DE-A 23 33 634 describes a process for preparing alkali metal and alkaline earth metal alkoxides which are free from alcohol of crystallization and are soluble in inert solvents by reacting alcohols such as iso alcohols, carbinols, secondary, tertiary and primary alcohols with alkali metals or alkaline earth metals in equimolar amount or in excess. The reaction takes place in an inert solvent under superatmospheric pressure and at temperatures at which, under atmospheric pressure, alcohol of crystallization would be eliminated. Since within this temperature/pressure range the alkali metal is in molten form it is easy to disperse, thereby achieving an increased reaction rate, and it can be added in fairly large pieces. Nevertheless, the reaction times are relatively long. The super-atmospheric pressure necessitates the use of pressure apparatus, which entails additional costs. The excess of metal employed with preference leads, after two or more reactions, to an accumulation of impurities, which may disrupt the reaction and which necessitate cleaning operations.

DE-C 26 12 642 diskloses a process for preparing alkali metal alkoxides which are free from alcohol of crystallization and are soluble in inert solvents by reacting tertiary alcohols such as tert-butyl alcohol and tert-amyl alcohol with stoichiometric amounts of alkali metal. The reaction is conducted in an inert solvent at a temperature above the melting point of the alkali metal and below the elimination temperature of the alcohol of crystallization. In order to increase the reaction rate the alkali metal is in dispersed form (particle size <100 $\mu$m). Here again, the reaction of tert-butanol, for example, must be conducted under super-atmospheric pressure.

DD 298 502 describes a process for preparing alkali metal alkoxides which are free from alcohol of crystallization, by reacting alcohols, including tertiary alcohols, preferably in a slight excess, with alkali metals in an inert solvent. The reaction takes place at a temperature at which the alkali metal is in molten form and the alcohol is in vapor form. The alcohol is continuously recondensed and recycled to the reaction mixture.

JP-A 05 170680 (=DW93/252679) diskloses a process for preparing sodium tert-butoxide which is free from alcohol of crystallization by reacting tert-butyl alcohol with sodium, with the addition of from 5 to 15% by weight of an inert solvent, at a temperature of from 130 to 135° C. In this process the molten sodium is sprayed into the reaction mixture. Excess alcohol and solvent are removed by distillation. This process is highly complex. Moreover, the nozzles that are required are easily blocked, so that the process is susceptible to faults.

EP-A 0 749 947 diskloses a continuous process for preparing $C_4$ to $C_8$ sodium alkoxides. In this process a dispersion of sodium in an inert solvent is reacted at elevated temperature (from 100 to 140° C.) with from 0.4 to 0.6 times the molar amount of alcohol. From the resultant two-phase reaction mixture the upper phase, containing inert solvent and alkoxide, is decanted off and the lower phase, containing excess sodium, is admixed with fresh sodium and reacted again. A disadvantage of this process is that the reaction product has to be decanted off, which is awkward.

All of the abovementioned processes require additional high-boiling inert solvent. The removal of the solvent is generally laborious and, furthermore, is incomplete in the majority of cases. These additional impurities may be a disruption if the alkoxides are used, for example, in pharmaceutical syntheses. Furthermore, the use of an additional solvent gives rise to further costs for the purification of the solvent, for storage tanks and supply lines, etc. The alcohols obtained are normally used further directly as solutions in the corresponding inert solvents. To obtain solid alkoxides it is necessary to transfer the solutions to a drier, for example, and to free them from the solvent.

EP-A 0 192 608 describes a process for preparing alkali metal alkoxides of tertiary alcohols by reacting an alkali metal with a tertiary alcohol without adding inert solvents. In this case the hot alcohol is added with stirring to the molten alkali metal. The alcohol is employed in a 3–6-fold, preferably a 5-fold, molar excess. This process has the disadvantage that alcohols having boiling points below the melting point of the alkali metal that is employed cannot be reacted at a sufficient reaction rate, since the solid alkali metal cannot be dispersed adequately in the solvent. The alkali metal alkoxides obtained are used further directly in alcoholic solution.

It is an object of the present invention to provide a process for preparing alkali metal alkoxides which requires no additional high-boiling solvents and in which alcohols, especially slow-to-react alcohols with boiling points below the melting point of the alkali metal that is employed, such as tert-butanol, can be reacted completely with alkali metals. The reaction should take place very rapidly and under atmospheric pressure, and the alkali metal alkoxides should be obtained free from alcohol of crystallization. Moreover, it should be made possible to obtain the alkali metal alkoxides in solid form without great apparatus expenditure.

We have found that this object is achieved by a process for preparing alkali metal alkoxides by reacting alkali metals with alcohols in the presence of a catalyst.

The process of the invention allows rapid and complete reaction even of slow-to-react alcohols, such as tertiary alcohols, at below the melting point of the respective alkali metal under atmospheric pressure. The use of high-boiling solvents and expensive pressure apparatus is unnecessary. As a result, the process provided is cost-effective, economic, and simple to carry out.

The catalysts employed are generally solid catalysts, preferably in the form of their alcoholic solutions. It is preferred to employ transition metal salts.

Particularly suitable transition metal salts are salts of metals from sub groups 4 to 8 of the Periodic Table of the Elements. Particular preference is given to the use of salts of Fe, Ni, Cr, Ti, Co, Pt, Pd, V, Nb, W, Mo or Mn and of Rh or Ru. The use of iron salts is especially preferred.

Salts of Zn, Cu, Ag or Au may also be used.

Examples of suitable salts are chlorides, bromides, iodides, nitrates, acetates, formates, oxalates and other carboxylates, complexes of β-diketones and β-ketocarboxylic acid derivatives, and also alkoxides. Chlorides are preferably employed.

Iron(III) octoate, titanium tetrabutylate or iron(III) chloride may be used, for example, as catalysts.

The use of iron(III) chloride as catalyst is especially preferred.

The transition metal salt is employed preferably in very small amounts, within the ppm range. The amount used is 1–1000 ppm, preferably 10–100 ppm, calculated as metal and based on the amount of alkali metal employed. When using iron(III) chloride as catalyst, for example, between 30 and 300 mg of iron(III)chloride are employed per kg of sodium.

The reaction of the alkali metal with the alcohol in accordance with the invention takes place preferably without additional solvent. The alcohol in question is preferably employed in excess and serves simultaneously as dispersion medium and solvent. The level of the excess of alcohol is generally dependent on the solubility of the alkoxide in the alcohol in question. Normally, the molar ratios of alcohol to alkali metal are chosen so as to give a stirrable suspension of the alkoxide in the alcohol. The alcohol is generally employed in an at least 2-fold molar excess. Preference is given to an at least 5-fold molar excess of the alcohol over the alkali metal employed, and particular preference is given to a 5–10-fold molar excess.

The process of the invention is suitable for all types of alcohols. Primary, secondary and tertiary alcohols can be employed. This process can be employed with particular advantage to react alcohols which are slow to react. Such alcohols are, in particular, tertiary alcohols, preferably those having 4 to 10 carbon atoms, and with particular preference tert-butanol and tert-amyl alcohol. The application of the process of the invention with slow-to-react alcohols with boiling points below the melting point of the alkali metal that is employed is especially advantageous. Therefore, it is especially preferred to employ tert-butanol. An example is the preparation of sodium tert-butoxide from sodium (melting point 98° C.) and tert-butanol (boiling point 82° C.).

The process is also successful in the case of low-boiling slow-to-react alcohols, without additional high-boiling solvent or the application of pressure.

The alcohol can be reacted with the alkali metal at a temperature below the melting point of the alkali metal. Preferably, the reaction is conducted at or close to the boiling point of the respective alcohol. For example, the reaction of tert-butanol with sodium is conducted in boiling tert-butanol, which corresponds to a temperature of approximately 82° C.

All alkali metals are suitable in principle as the alkali metal. Preference is given to employing Li, K or Na, particular preference to K or Na, and very particular preference to Na.

A particular advantage of the process of the invention is evident in this. In the reaction of low-boiling slow-to-react alcohols it is possible to employ the inexpensive sodium despite its high melting point in comparison to the more expensive potassium. As a result, the process of the invention is highly cost-effective.

In one preferred embodiment the alkali metal is first of all metered in liquid form into a mixture of alcohol and catalyst. When sodium is used it is heated to about 120–130° C. so as to form a melt. This melt is added dropwise with stirring to the reaction mixture, or the melted sodium is allowed to run in as a thin jet. In the process of the invention there is no need for particularly fine distribution of the alkali metal. Suitable particles generally have average diameters of between 1 and 10 mm. The reaction temperature preferably lies within the region of the boiling point of the respective alcohol.

The process of the invention is also suitable for reacting alcohols, especially tertiary alcohols, with a boiling point above the melting point of the alkali metal, by choosing a temperature above the melting point. Here again, the use of the catalyst results in a reduction in the reaction times and therefore in the batch times too.

When reacting tert-amyl alcohol with sodium, for example, it is therefore possible to operate at the boiling point of the alcohol (about 102° C.). At this temperature, the sodium is liquid and is dispersed with the stirrer. Under these conditions, the reaction time depends on the stirrer speed and on the nature and concentration of the catalyst. In this system, high speeds lead to good dispersing and so to a rapid reaction, which can be accelerated further by adding the catalyst of the invention.

The duration of the reaction is dependent, inter alia, on the batch size, on the alcohol employed and on the alkali metal that is employed. The reaction is monitored by way of the hydrogen that is liberated. The end of hydrogen evolution indicates the end of the reaction of the alcohol with the alkali metal.

The reaction can be conducted in solution or in a suspension. In this context it is preferably conducted so as to give a suspension of the alkoxide in the corresponding alcohol. In such a system, a large proportion of the alkoxide is also present in dissolved form.

In the preparation of sodium tert-pentoxide, in one preferred embodiment, a solution of the alkoxide in the corresponding alcohol is obtained first of all. Since the solubility of sodium tert-pentoxide in amyl alcohol is quite high, at from about 30 to 35% by weight at 100° C., reaction in a suspension is unnecessary in this case.

The preferred product concentration of the alkoxide in the corresponding alcohol is dependent on the alcohol employed and on the solubility of the corresponding alkoxide in the alcohol. Depending on the alcohol used, product concentrations of up to 60% by weight of alkoxide in the corresponding alcohol are possible. In the case of the preparation of sodium tert-butoxide a product concentration of 20–30% by weight of tert-butoxide in tert-butanol is preferred, with particular preference being given to around 15% by weight.

The alkoxides prepared are generally obtained in solid form as alkoxides which are free from alcohol of crystallization. These alkoxides, depending on their structure and chain length, are soluble in numerous solvents and can be employed in a host of reactions.

In one preferred embodiment, the alkali metal alkoxides are obtained in solid form, free from alcohol of crystallization, following the reaction by evaporating if necessary to remove excess alcohol, and drying.

The evaporation of the excess alcohol and drying of the resultant solid are carried out, in general, at a temperature above the boiling point of the alcohol used, following the reaction.

Depending on the alcohol used, the alkoxides are dried generally at a temperature in the range 90–230° C., preferably 100–200° C. and, with particular preference, 110–180° C., under atmospheric pressure.

By applying a subatmospheric pressure of generally up to not more than 200 mbar, preferably 10–100 mbar and, with particular preference, 10–30 mbar, drying can be accelerated and the drying effect improved. Furthermore, when using subatmospheric pressure, it is possible to go below the stated temperature ranges. The temperature and subatmospheric pressure should be chosen so as to minimize the sublimation losses of the alkoxide.

With particular preference, reaction, evaporation, and drying are conducted in a single apparatus.

The prior art processes for preparing alkali metal alkoxides free from alcohol of crystallization relate to the preparation of the alkali metal alkoxides in solution. The solvent in those processes is generally an inert, high-boiling solvent. To obtain solid alkali metal alkoxides, these solutions must be transferred to a separate apparatus suitable for evaporation and drying. The use of a plurality of apparatuses, however, leads to high capital investment costs and also to additonal worksteps, which make the product more expensive.

Reactors suitable for preparing solid alkali metal alkoxides free from alcohol of crystallization, in accordance with the process of the invention, in a single apparatus are those which very largely prevent the deposition of solid alkali metal alkoxide on the reactor walls and are suitable for effective mixing of the reaction mixture. Use is therefore made preferably of reactors having a close-clearance stirring element. The stirrer-to-wall distance is generally from 0.1 to 5 cm, preferably from 0.1 to 1 cm, with particular preference from 0.1 to 0.8 cm.

Particular preference is given to using reactors having stirring elements in which Froude numbers of >0.1, preferably >0.5, with particular preference >1.0, may be realized.

The Froude number is a measure of the intensity of mixing and is defined as $$Fr = \frac{(2\pi f)^2 \cdot r}{g}$$

where
g is acceleration due to gravity [9.81 m/s$^2$]
r is radius [m]
f is frequency [1/s].

The frequency is determined from the speed of the mixing tools. The radius is the greatest distance between the mixing tool and the shaft.

Suitable types of reactor or mixer are selected, for example, from List dryers (e.g., Diskotherm reactor), stirred vessels with anchor stirrer, paddle dryers, stirred vessels with helical stirrer, plowshare mixers (Lodige mixers) and Eirich mixers.

For the purposes of the present invention, a paddle dryer is a cyclindrical reactor which is generally arranged horizontally. Within this reactor, paddles (stirring element) rotate on a horizontal shaft. The paddle-to-wall distance is low—at least in the bottom region—so that relatively thick wall deposits are prevented.

List dryers may be single-shaft (e.g., Diskotherm reactor) and twin-shaft apparatuses whose distinguishing feature is that they have not only stirring elements located on the main shaft but also counterhooks on the wall (single-shaft apparatus) and/or a second shaft with "cleaning hooks". These hooks or cleaning shafts exhibit intensive inter-engagement for the purpose of mixing or kneading the product and for cleaning the product-contacted surfaces, which is necessary in particular in the case of pastelike or incrusting products so as to suffer no restrictions in heat passage.

A stirring vessel with anchor stirrer may comprise, for example, an angle-axis anchor stirrer, i.e., a stirring element which is at a small distance from the wall. The anchor stirrer provides for effective mixing of a batch. Owing to the close wall clearance it prevents the growth of relatively thick crusts on the wall. Accordingly, such an apparatus is also suitable for evaporation and drying.

A plowshare mixer (Lodige mixer) is a horizontal cylindrical reactor. Around a horizontal shaft there rotate mixing tools having a form which resembles that of the plows used in agriculture. The distance of the mixing tool from the wall is small.

The Eirich mixer is a mixer in which an obliquely disposed mixing trough rotates. Caking on the walls is prevented by a wall scraper which in this case is fixed, since the container rotates.

The corresponding stirring elements are generally operated at speeds of from 5 to 500 rpm, preferably from 5 to 200 rpm, with particular preference from 10 to 100 rpm.

In addition to the stirring element which is used, the reactors preferably comprise a further stirring or comminuting element. This element is generally operated, depending on the size of the reactors and on the stirring and comminuting elements used, at speeds of from 500 to 20 000 rpm, preferably from 1000 to 10 000 rpm, with particular preference from 1000 to 5000 rpm. The Froude numbers obtained with this stirring element are usually >1. The further stirring or comminuting element is used to produce high shear fields, by means of which caking together of the alkali metal and caking together or caking to the reactor walls of the alkali metal alkoxide which has been formed and which may have undergone partial precipitation from the solution (i.e., is present in suspension) are prevented even at temperatures below the melting point of the alkali metal. Furthermore, alkali metal alkoxide crusts on the alkali metal are removed.

As a result, a particularly high reaction rate of the reactants is achieved, so that only very small amounts of catalyst are necessary.

In general, the efficiency of the stirring or comminuting element goes up as the rotary speed increases. At some point in time, however, a region is reached in which a further increase no longer brings any advantages and a further increase is no longer economic. Furthermore, the rotary speed range must be chosen so that no cavitation occurs (which may be the case at very high speeds). Optimum speeds must be found for the particular type of reactor used and for the selected combination of the stirring elements, in routine tests.

Suitable additional stirring or comminuting elements are in particular, as a function of the stirring or mixer types used, blade mills, choppers, dissolver disks, disk stirrers, inclined-blade stirrers, Turrax® or Ultraturrax® stirrers, or swirlers.

In accordance with the present invention, blade mills are rapidly rotating blades which ensure comminution of solids.

Dissolver disks are high-speed rotary disks with jagged edges. A disk stirrer is a rotating disk with two or more stirring blades mounted on the edge, and an inclined-blade stirrer has a plurality of stirring blades mounted at an inclination on the edge and/or on the shaft. These stirring or comminuting elements are generally high-speed rotary stirrers which are able to produce high shear fields.

Swirlers are whirlerlike or stirrerlike mixing tools which can have diverse geometric shapes and which ensure effective mixing and the introduction of a high mixing energy.

Particularly preferred combinations of reactor or mixer types and stirring or comminuting elements are selected from the following: paddle dryer with additional blade mills in the bottom region of the paddle dryer; List dryers, which may be both single-shaft (Diskotherm reactors) and twin-shaft; stirring vessels with anchor stirrer or helical stirrer and at least one, preferably 2 to 4, with particular preference 3 to 4, dissolver disks or with disk stirrer, inclined-blade stirrer, Turrax® stirrer or Ultraturrax® or blade mills; plow-share mixers (Lodige mixers) with built-in chopper; Eirich mixers, in which wall caking is prevented by a wall scraper and the shear fields are applied by swirlers.

The Eirich mixer is an intensive mixer which is characterized by a rotating mixing vessel and an optionally co- or counter-rotating mixing tool (swirler). The mixing tool may attain a very high rotary speed of more than 2000 rpm. The mixing tools comprise whirlerlike or stirrerlike tools which can have diverse geometric shapes and which ensure effective mixing and the introduction of a high mixing energy. A wall scraper prevents material caking on the wall. Eirich intensive mixers are available from Maschinenfabrik Gustav Eirich, Hardheim, Germany.

The process may also be conducted with preference in a heatable vacuum mixer. Vacuum mixers are available, for example, from Eirich. These mixers operate in accordance with the so-called EVACTHERM® process (from Eirich).

In another embodiment of the present invention, instead of a second stirring or comminuting element disposed in the reactor, it is possible to use an external comminuting element for a wet comminution. In this embodiment, the contents of the reactor are pumped in circulation through this apparatus. Preferred external comminuting elements are wet rotor mills or toothed wheel dispersion machines and stirred mills.

Where solid alkali metal alkoxides free from alcohol of crystallization are prepared in a single apparatus, the reaction of alkali metal with the alcohol is preferably conducted at a temperature below the melting point of the alkali metal used. This embodiment of the process of the invention is therefore particularly suitable for preparing solid alkali metal alkoxides, free from alcohol of crystallization, whose corresponding alcohol component has a boiling point below the melting point of the alkali metal used. Very particular preference is given, therefore, to the preparation of Na tert-butoxide from tert-butanol (boiling point: 82° C.) and sodium (melting point: 98° C.). The process is normally conducted at atmospheric pressure.

In order to implement this embodiment of the process of the invention, the corresponding alcohol, preferably tert-butanol, is introduced into an appropriate reactor together with the catalyst used in accordance with the invention, preferably iron(III) chloride, and melted alkali metal, preferably sodium, is metered into the initial reaction mixture charge at atmospheric pressure by way of a nozzle or an inlet pipe. Metering is preferably conducted in such a way that the temperature of the alcohol is below the melting point of the alkali metal. As a result of the low temperature, the alkali metal metered in solidifies to form beads and reacts with the alcohol to form the corresponding alkali metal alkoxide. The stirring elements of the stirrer ensure intensive mixing of the reaction mixture. Mixing is further improved, preferably, by using a second stirring or comminuting element, thereby making it possible to achieve a further increase in the reaction rate. After the end of the evolution of hydrogen that occurs during the reaction, the reactor is heated to temperatures of generally 90–230° C., preferably 100–200° C., with particular preference 110–180° C., at atmospheric pressure. If a reduced pressure of generally up to max. 200 mbar, preferably 10–100 mbar, with particular preference 10–30 mbar, is applied, the temperature ranges may be less than those stated. The temperature and the reduced pressure are to be selected so that, as far as possible, little if any losses occur by sublimation of the alkoxide. The excess alcohol is removed in this way to give a solid alkoxide, free from alcohol of crystallization, in a purity of generally >98%, preferably >99%. This alkoxide may be used directly in further reactions.

Where the preparation of solid alkali metal alkoxides free from alcohol of crystallization is conducted in a single apparatus, it is preferred to use an apparatus comprising:
a) a heatable reactor A having a close-clearance stirring element,
b) a means B of adding liquid alkali metal to the reactor,
c) a condenser C for recycling to the reactor alcohol evaporated during the reaction, by way of which excess alcohol distilled off during the evaporation and drying which takes place subsequent to the reaction may be condensed out,
d) a further stirring or comminuting element D.

Corresponding suitable reactors A, which may also have a means of applying reduced pressure, and also suitable second stirring and comminuting elements, have already been described above.

The means B of adding liquid alkali metal to the reactor preferably comprises a heatable container from which the liquid alkali metal is metetered into the reactor via a pipe, a tap or a pipe with a tap. e.g., a heatable dropping funnel. Metering may take place by means of gravity, by means of inert gas overpressure, or using a pump, for example.

As the condenser C it is possible to use virtually any type of condenser.

FIG. 1 depicts diagrammatically a preferred embodiment of a suitable apparatus. In the figure:
A is a heatable reactor having a close-clearance stirring element, exemplified by a stirred vessel with anchor stirrer;
B is a means of adding liquid alkali metal;
C is a condenser;
D is a further stirring or comminuting element, exemplified by 3 dissolver disks.

The present invention additionally provides for the use of a catalyst, preferably a transition metal salt and, with very particular preference, iron(III) chloride, in the preparation of alkali metal alkoxides from alkali metals and alcohols.

By this means it is possible to conduct the reaction of alcohols, especially alcohols which are slow to react tertiary alcohols with low boiling points, under atmospheric pressure and without additional high-boiling solvent within short reaction times. Complex apparatus for operating under pressure is unnecessary.

The examples which follow illustrate the invention.

EXAMPLE 1

4400 g of tert-butanol were charged to a 5 l stirred reactor with built-in flow disrupters, reflux condenser and blade stirrer (rotary speed: 200 rpm), this initial charge was heated to boiling point, and 2 ml of an approximately 2% strength by weight solution of $FeCl_3*6H_2O$ in tert-butanol were added. Sodium (160 g) was cut bright in a nitrogen cabinet, placed in a heated jacketed dropping funnel and heated to 120–130° C. to form a melt. Over the course of 10–15 minutes the sodium in liquid form was added dropwise to the stirred mixture (drop diameter approximately 1–5 mm). Vigorous reflux ensued. The reaction was monitored by means of the hydrogen which was evolved. After a run time of about 4 hours there was no longer any measurable evolution of gas, and a suspension had formed. The reaction was at an end. Subsequently, samples were taken for titration (about 4 ml of suspension) and were weighed out into water. Titration with hydrochloric acid gave a concentration of 14.5% by weight of sodium tert-butoxide (solubility of sodium tert-butoxide in tert-butanol is <10%). The resultant suspension was transferred while still hot into a 5 l paddle drier and was concentrated by evaporation and dried under atmospheric pressure at a jacket temperature of 150° C. This gave 650 g of solid sodium tert-butoxide with a purity of >99%.

EXAMPLE 2

Comparative

As in the above example, sodium and tert-butanol were reacted with one another, except that no catalyst was added. Following the addition of the sodium, a large lump of sodium was formed. After about 6–8 hours a thick suspension had formed which still contained significant amounts of sodium pellets. These pellets were partially incrusted and reacted only very slowly. The experiment was terminated after 10 hours. At this point in time, the sodium had still not fully reacted.

EXAMPLE 3

Preparation of Sodium Tert-pentoxide 4400 g of tert-amyl alcohol were charged to a 5 l stirred vessel with built-in flow disrupters and a disk stirrer, this initial charge was heated to boiling at about 102° C., with stirring, and 2 ml of an approximately 2% strength solution of $FeCl_3*6H_2O$ in tert-butanol were added.

Sodium (300 g) was placed in a heated jacketed dropping funnel and heated to from 120 to 130° C. to form a melt. Over the course of 45 minutes the sodium in liquid form was added to the stirred mixture (stirrer speed: 800 rpm). At this temperature, sodium remained liquid and was dispersed with the stirrer. Vigorous reflux ensued. The reaction was monitored by means of the hydrogen which was evolved. After a post-reaction period of 1 hour there was no longer any measurable evolution of gas. The reaction was at an end. The resultant clear solution was drained off while still hot through the bottom valve into a rotary evaporator and was concentrated by evaporation and dried at a bath temperature of 130° C. under a subatmospheric pressure of about 30 mbar.

This gave 1.4 kg of solid sodium tert-pentoxide with a purity of >99%. The concentration of NaOH was <1%.

EXAMPLE 4

Comparative

The reaction of Example 3 was repeated but without addition of catalyst. In this case, at the same stirrer speed, the reaction did not end until after 6 hours.

EXAMPLE 5

A 5 l stirred reactor equipped with a close-clearance, angle-axis anchor stirrer and three dissolver disks (on a shaft), jacket, jacket dropping funnel and internal thermometer was charged with 5 l of tert-butanol which was heated to boiling temperature with stirring (b.p.: 82.5° C.). The anchor stirrer rotated at 90 rpm and the dissolver disks at 2000 rpm. 28 mg of $FeCl_3$ were added to the t-butanol, sodium (215 g) was cut bright in a nitrogen cabinet, placed in the jacket dropping funnel and melted by heating at 130° C. under nitrogen (m.p.: 97.8° C.). The sodium in liquid form was added dropwise over 10–60 minutes (drop diameter approximately 1–10 mm). The reactor contents were stirred at boiling temperature for 6–8 h (until evolution of hydrogen was at an end). Subsequently, the temperature of the heat transfer medium was increased and t-butanol was distilled off. The product was subsequently dried by increasing the wall temperature to 180° C. If necessary, drying was assisted by the application of reduced pressure. 860 g of Na tert-butoxide were diskharged.

Alkoxide purity: >98% a NaOH content: <1.5%

Residual amount of unreacted sodium: <10 ppm

EXAMPLE 6

A 5 l laboratory paddle dryer was charged with 2414 g of t-butanol and 0.0176 g of $FeCl_3$ which was heated to approximately 75–80° C. 130 g of sodium were melted in a jacketed dropping funnel and subsequently metered in liquid form into the paddle dryer. After the end of reaction (about 11 h) the jacket temperature of the dryer was slowly increased to 180° C., excess t-butanol was distilled off, and the alkoxide was dried. Approximately 500 g of sodium tert-butoxide (purity: >99%) were diskharged from the paddle dryer.

We claim:

1. A process for preparing alkali metal alkoxides by reacting alkali metals with tertiary alcohols, wherein the reaction takes place in the presence of a transition metal salt as catalyst.

2. A process as claimed in claim 1, wherein iron(III) chloride is employed as catalyst.

3. A process as claimed in claim 1, wherein the transition metal salt is employed in an amount of 1–1000 ppm calculated as metal and based on the amount of alkali metal employed.

4. A process as claimed in claim 1, wherein the alcohol is employed in excess and serves simultaneously as dispersion medium and solvent.

5. A process as claimed in claim 1, wherein tert-butanol or tert-amyl alcohol is employed.

6. A process as claimed in claim 1, wherein the reaction is conducted at or close to the boiling point of the respective alcohol.

7. A process as claimed in claim 1, wherein sodium is employed as the alkali metal.

8. A process as claimed in claim 1, wherein the reaction is conducted so as to give a suspension of the alkoxide in the corresponding alcohol.

9. A process as claimed in claim 1, wherein the alkali metal alkoxides are obtained in solid form, free from alcohol of crystallization, following the reaction by optional evaporation of excess alcohol and drying.

10. A process as claimed in claim 8, wherein the reaction, evaporation, and drying are conducted in a single apparatus.

11. A process as claimed in claim 10, wherein the apparatus is a reactor having a close-clearance stirring element.

12. A process as claimed in claim 11, wherein reactors used comprise reactor types or mixer types selected from paddle dryers, Diskotherm reactors (List dryers), stirred vessel with anchor stirrer, stirred vessels with helical stirrer, plowshare mixers (Loedige mixers), and Eirich mixers.

13. A process as claimed in claim 12, wherein the reactor used is a paddle dryer or a stirred vessel with anchor stirrer.

14. A process as claimed in claim 10, wherein in addition to the stirrer the apparatus has a further stirring or comminuting element.

15. A process as claimed in claim 14, wherein the further stirring or comminuting element is selected from blade mills, choppers, dissolver disks, disk stirrers, inclined-blade stirrers, Turrax stirrers or Ultraturrax.

16. A process as claimed in claim 15, wherein the further stirring or comminuting element is an external comminuting unit for wet comminution.

* * * * *